United States Patent
Jiang et al.

(10) Patent No.: US 6,556,306 B2
(45) Date of Patent: Apr. 29, 2003

(54) DIFFERENTIAL TIME DOMAIN SPECTROSCOPY METHOD FOR MEASURING THIN FILM DIELECTRIC PROPERTIES

(75) Inventors: Zhiping Jiang, Ottawa (CA); Ming Li, Cupertino, CA (US); Xi-Cheng Zhang, Latham, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 190 days.

(21) Appl. No.: 09/754,183

(22) Filed: Jan. 4, 2001

(65) Prior Publication Data
US 2002/0118371 A1 Aug. 29, 2002

(51) Int. Cl.$^7$ ................................................. G01B 9/02
(52) U.S. Cl. ....................................... 356/517; 356/487
(58) Field of Search ................................ 356/517, 491, 356/450, 128, 484, 487, 485

(56) References Cited

U.S. PATENT DOCUMENTS

| | | |
|---|---|---|
| 4,968,136 A | 11/1990 | Lim et al. |
| 5,034,617 A | 7/1991 | Isobe |
| 5,056,111 A | 10/1991 | Duling, III et al. |
| 5,376,888 A | 12/1994 | Hook |
| 5,381,234 A | 1/1995 | Barbee et al. |
| 5,502,392 A | 3/1996 | Arjavalingam et al. |
| 5,548,404 A | 8/1996 | Kuperschmidt et al. |
| 5,726,578 A | 3/1998 | Hook |
| 5,798,837 A | 8/1998 | Aspnes et al. |
| 5,818,582 A | 10/1998 | Fernandez et al. |
| 5,872,447 A | 2/1999 | Hager, III |
| 5,889,592 A | 3/1999 | Zawaideh |
| 5,946,096 A | 8/1999 | Lee et al. |
| 6,057,928 A | 5/2000 | Li et al. ...................... 356/495 |
| 6,075,928 A * | 5/2000 | Li et al. ...................... 356/454 |

OTHER PUBLICATIONS

"Optoelectronic Transient Characterization of Ultrafast Devices" by M. Y. Frankel et al. IEEE Journal of Quantum Electronics, vol. 28, No. 10. 10/92. pp. 2313–2324.

(List continued on next page.)

Primary Examiner—Samuel A. Turner
Assistant Examiner—Patrick Connolly
(74) Attorney, Agent, or Firm—RatnerPrestia (57) ABSTRACT

A non-contact, free-space method for determining the index of refraction of a thin film at a desired angular frequency. The method includes generating an input desired-frequency pulse and an optically detectable probe pulse. The thin film is moved in and out of the path of the input pulse, creating an output pulse that alternates between a transmitted signal, created when the film intercepts the input pulse path, and a reference signal, created when the sample is outside the input pulse path. The output pulse modulates the probe pulse, which is then detected with a photo detector, and the difference between the transmitted signal and the reference signal is calculated. The above steps are repeated over a plurality of delay times between the input pulse and the probe pulse until a complete field waveform of the differential signal is characterized. The index of refraction is calculated as a function of a ratio between the differential signal for the thin film and the reference signal. A complete field waveform of the reference signal may be characterized by repeating the above steps for a reference plate identical to the sample except having a non-transmissive film instead of the thin, transmissive film.

10 Claims, 5 Drawing Sheets

OTHER PUBLICATIONS

"Optoelectronic On–Chip Characterization of Ultrafast Electric Devices: Measurement Techniques and Applications" by T. Pfeifer et al. IEEE Journal of Selected Topics in Quantum Electronics. vol. 2, No. 3, 9/96. pp. 586–603.

"Coherent broadband microwave spectroscopy using picosecond optoelectronic antennas" by Y. Pastol et al. Appl. Phys. Lett. 54 (4), Jan. 23, 1989. pp. 307–309.

"Far–infrared time–domain spectroscopy with terahertz beams of dielectrics and semiconductors" by D. Grischkowsky et al. J. Opt. Soc. Am. B/vol. 7, No. 10. 10/90. pp. 2006–2015.

"A Reliable Method for Extraction of Material Parameters in Terahertz Time–Domain Spectroscopy" by L. Duvillaret et al. IEEE Jor. Sel. Top. in Quantum Elec. 09/96. pp. 739–745.

"Gas spectroscopy measurements using a compact terahertz system" by G. Sucha et al. Proceedings of VSJ–SPIE98. Dec. 6, 1998. pp. 1–3.

"Portable THz system and its applications" by M. Li et al. Proceedings of SPIE 3616, submitted 1998.

"Design and Characterization of Traveling–Wave Electrooptic Terahertz Sensors" by Q. Wu et al. IEEE Jour. Sel. Topics in Quantum Elec. vol. 2, No. 3, 9/96. pp. 693–700.

"Principles of Optics" $6^{th}$ Ed. by M. Born et al. 1980. pp. 38–41.

* cited by examiner

DIFFERENTIAL TIME DOMAIN SPECTROSCOPY METHOD FOR MEASURING THIN FILM DIELECTRIC PROPERTIES

TECHNICAL FIELD

The present invention relates generally to measurement of dielectric properties of thin films on substrates and, more specifically, to determination of the index of refraction and the dielectric constant of a thin polymer film on a substrate in the gigahertz (GHz) to terahertz (THz) frequency range.

BACKGROUND OF THE INVENTION

In modern microcircuits, the high-frequency capacitance of interlevel dielectrics is a critical parameter that must be understood for realization of high-speed (clock speed>1 GHz) electronic devices. The characterization of the high-frequency dielectric properties of interlevel dielectrics is thereby crucial, particularly in the gigahertz (GHz) to terahertz (THz) range. To bridge electronic and optical gaps formerly encountered in the measurement of the dielectric constant in the GHz-THz frequency range, time-domain spectroscopy (TDS) techniques that incorporate ultrashort laser pulses have been developed in recent years for microcircuit test devices.

For characterization of low dielectric constant materials before circuitization, however, a conventional free-space, non-contact measurement is the most convenient and low-cost method. For this purpose, a time-domain coherent technique has been demonstrated in the far-infrared (FIR) range that has been shown to be a promising alternative to the conventional electronic or continuous wave method. Boosted by the rapid development of a compact and portable femtosecond (fs) laser system, time-domain FIR techniques using all room-temperature components have become attractive for a number of industrial applications, including, but not limited to, gas spectroscopy, measurement of conductivity, study of the dynamics of semiconductor materials, and measurement of water concentration in biological samples. With extremely flat frequency response, large dynamic range, and excellent signal-to-noise ratio (SNR), free-space electro-optic sampling (FS-EOS) has emerged as a coherent terahertz detection technique capable of detecting amplitude, phase, and spacial distribution information in a terahertz beam. For example, the refractive index and dielectric constant of thin films has been measured by inserting the film into a THz beam and comparing the Fourier transforms of the THz waveforms obtained with and without the thin film.

For free-space dielectric constant measurement of the film on a substrate, where the thickness of the film is much thinner than the wavelength of the applied electromagnetic (EM) waves, the free-space time-domain technique has a fundamental restriction. The principle of the coherent free-space technique for measurement of the dielectric constant is based on the evaluation of the relative phase shift due to the index of refraction, the index of refraction being the square-root of the dielectric constant. For a film much thinner than the wavelength used for measurement, the visibility of the small phase shift in the waveform is difficult to obtain under realistic experimental conditions. For instance, for 100 GHz EM waves refracted through a one-micrometer film, a phase change on an order of only $10^{-3}$ radians is expected. This phase difference is extracted by comparing a first waveform refracted through the thin film on a substrate against a second, reference waveform refracted from the substrate without the film. Under most experimental conditions, this extraction is often difficult due to the experimental uncertainty between two separate measurements. Thus, it is highly desirable to measure the phase difference in a single measurement.

U.S. Pat. No. 6,057,928, issued on May 2, 2000, to Ming Li et al., describes one method that avoids many of the problems in the prior art. That method requires measurements to be taken at multiple angles of reflection, however, which can be time consuming. The present invention proposes a differential time domain spectroscopy (DTDS) method that allows the measurement of dielectric properties on even thinner films and in less time than the method described in the '928 patent.

SUMMARY OF THE INVENTION

The present invention provides a non-contact method for determining in a free space the index of refraction ($n_2(\omega)$) at a desired angular frequency ($\omega$) of a sample comprising a thin, transmissive film which is optionally disposed on a substrate, the thin film having a thickness (d). The method comprises generating an input desired-frequency pulse and a probe pulse having wavelength and duration shorter than the input pulse, and directing the input pulse along a first path and the probe pulse along a second path. The sample is moved in and out of the first path, creating an output pulse which alternates between a transmitted signal ($E_{film}(\omega)$), created when the sample is in the path of the input pulse, and a reference signal ($E_{ref}(\omega)$), created when the sample is outside the input pulse path. The output pulse modulates the probe pulse, which is then detected with a photo detector, and a differential signal ($E_{diff}(\omega)$) for the thin film comprising a difference between the transmitted signal and the reference signal is calculated. The above steps are repeated over a plurality of delay times between the input pulse and the probe pulse until a complete field waveform of the differential signal for the thin film is characterized. The index of refraction is calculated as a function of a ratio between the differential signal for the thin film and the reference signal.

A complete field waveform of the reference signal may be characterized by repeating the above steps for a reference plate identical to the sample except comprising a non-transmissive film instead of the thin, transmissive film. Where the sample is mounted on a substrate, the non-transmissive film is mounted on an identical substrate. When repeating the above steps for the reference plate, the output pulse alternates between the reference signal ($E_{ref}(\omega)$), created when the non-transmissive film is outside the path of the input pulse, and an absence of a signal, created when the non-transmissive film is in the path of the input pulse. The differential signal calculated for the reference plate is thus equal to the reference signal.

The index of refraction is calculated to be:

$$n_2(\omega) = \sqrt{(n_{1+n_3)(1+A(\omega))) - n_{1n_3}}}$$

where:

$$A(\omega) = \frac{c}{\omega d} \left| \frac{E_{diff}(\omega)}{E_{ref}(\omega)} \right|$$

$n_1$ = index of refraction of the free space, and
$n_3$ = index of refraction of the optional substrate.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

Figure 1:
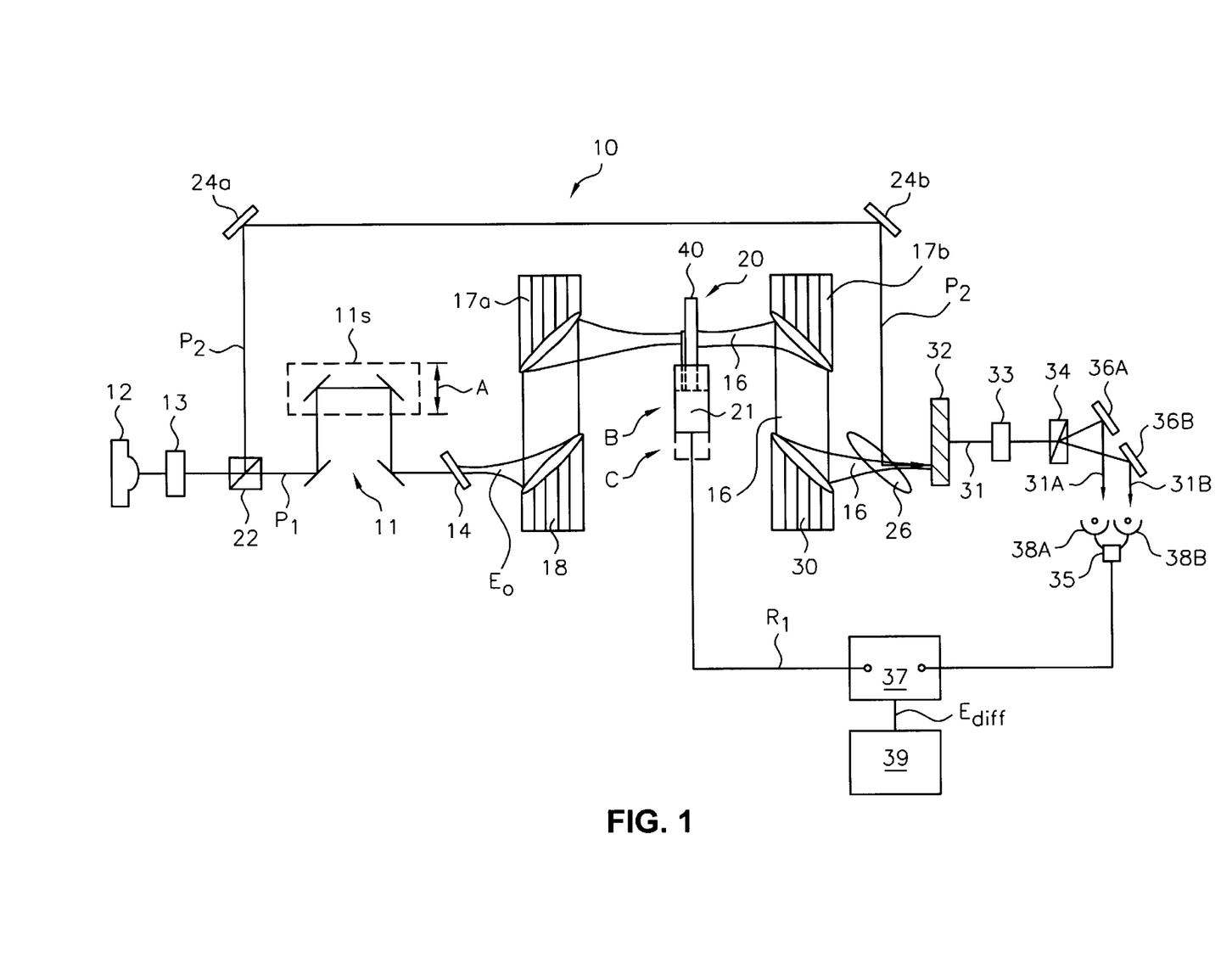
FIG. 1 is a schematic illustration of an exemplary system for performing the method of the present invention.

Referring now to the drawing, in which like reference numbers refer to like elements throughout, FIG. 1 schematically shows an exemplary EO sampling apparatus 10 for measuring the FIR dielectric constant of a thin film on a substrate. EO sampling techniques and general principles are known in the art for measuring THz pulses. Therefore, a detailed explanation of such techniques and principles is not provided as unnecessary.

As depicted in FIG. 1, an optical source 12 (such as a mode-locked titanium:sapphire ultrafast laser) generates a source pulse that is transmitted through a polarizer 13 and a polarizer beam splitter 22. The combined effect of polarizer 13 and polarizer beam splitter 22 provides a pump pulse $P_1$ and a probe pulse $P_2$.

$P_1$ comprises an illuminating optical excitation pulse that generates a beam of desired frequency when it hits an emitter 14. Emitter 14 may comprise, for example, a ZnTe crsytal that, when excited by pulse $P_1$, emits a THz radiation pulse $E_0$ using an optical rectification effect.

Emitter 14 emits radiation pulse $E_0$ of a desired-frequency, such as GHz-THz radiation, onto a first paraboloidal mirror 18. First paraboloidal mirror 18 collimates pulse $E_0$ and directs it toward a second paraboloidal mirror 17a that reflects and focuses the pulse toward a sample 20, which is located in the focal plane for mirror 17a. Sample 20 is mounted on a galvanometer 21, which vibrates sample 20 back and forth between a first position B, in which a thin film 42 is inside the path of pulse $E_0$, and a second position C (shown in dashed lines), in which thin film 42 is outside the path of pulse $E_0$. A vibration distance of about 5 mm is typically sufficient to move sample 20 completely in and out of the path of pulse $E_0$. When pulse $E_0$ is transmitted through thin film 42 and substrate 40, with sample 20 in position B, pulse $E_{film}$ is formed. When pulse $E_0$ is transmitted only through substrate 40, with sample 20 in position C, it forms pulse $E_{ref}$.

It should be noted here that sample 20 may comprise merely a sample of the thin film to be measured without a substrate, or may comprise the thin film mounted on a substrate. Where sample 20 comprises the thin film on a substrate, the thin film only covers a portion of substrate 40 such that, when sample 20 is in position C, the portion of substrate 40 not covered by sample 20 is still in the path of pulse $E_0$. Thus, where sample 20 comprises a thin film without a substrate, $E_{ref}$ comprises the signal created when pulse $E_0$ is transmitted through the free space alone.

Thus, an output pulse 16 comprising a signal, which alternates between $E_{film}$ and $E_{ref}$ at the frequency of vibration of galvanometer 21, is reflected off a third paraboloidal mirror 17b to a fourth paraboloidal mirror 30. Paraboloidal mirror 30 focuses output pulse 16 onto an electro-optical (EO) sensor 32, such as a <110> ZnTe crystal with a thickness of about 2 mm.

Probe pulse $P_2$ is reflected off a mirror 24a to a mirror 24b to a pellicle 26. Pellicle 26 is typically 2-to-4 microns thick such that the long wavelength of output pulse 16 allows it to pass through pellicle 26 without reflection. In EO sensor 32, the E-field of the output pulse tunes probe pulse $P_2$ by modulating it to include a component proportional to the output pulse. Thus, pulse 31 leaving EO sensor 32 contains information relating to pulse $P_1$.

A quarter waveplate 33, a Wollaston prism 34, and photodetectors 38A, 38B comprise a typical EO sampling system, which is known in the art. Mirrors 36A and 36B are optional, based upon the desired physical footprint of the system. The E-field of pulse $P_1$ induces birefringence inside the ZnTe crystal of EO sensor 32, which in turn changes the polarization of pulse $P_2$. The following optics and electronic circuitry extract this change.

Quarter waveplate 33 changes the linear polarization of pulse 31 to a circular polarization. Wollaston prism 34 splits the circular polarization of pulse 31 back into linearly polarized pulses 31A and 31B, each polarized 90° relative to the other. Each pulse 31A and 31B is reflected off mirrors 36A and 36B, respectively, onto photo detectors 38A and 38B, respectively, which may be photodiodes. Photo detectors 38A and 38B are connected to circuitry 35, known in the art, which subtracts the waveform of pulse 31B from the waveform of pulse 31A to eliminate the common current with reduced noise. The modulation of pulse $P_2$ by output pulse 16 within EO sensor 32 can be detected because the intensity components in pulses 31A and 31B proportional to the THz electric field have the same value but opposite sign. Thus, the change induced by output pulse 16 is doubled after subtraction of pulse 31A from pulse 31B.

The $P_1$-induced signal is then transmitted to a lock-in amplifier 37 that is synchronized to a reference signal $R_1$ from galvanometer 21. Lock-in amplifier 37 contains circuitry that produces the differential signal $E_{diff} \equiv E_{film} - E_{ref}$, which is output to a data acquisition system 39, such as a computer.

Between beam splitter 22 and emitter 14, pulse $P_1$ is directed through a delay stage 11. Delay stage 11 provides a variable distance through which pulse $P_1$ can travel by moving a stage 11s up and down along the direction of arrow A.

Figure 2:
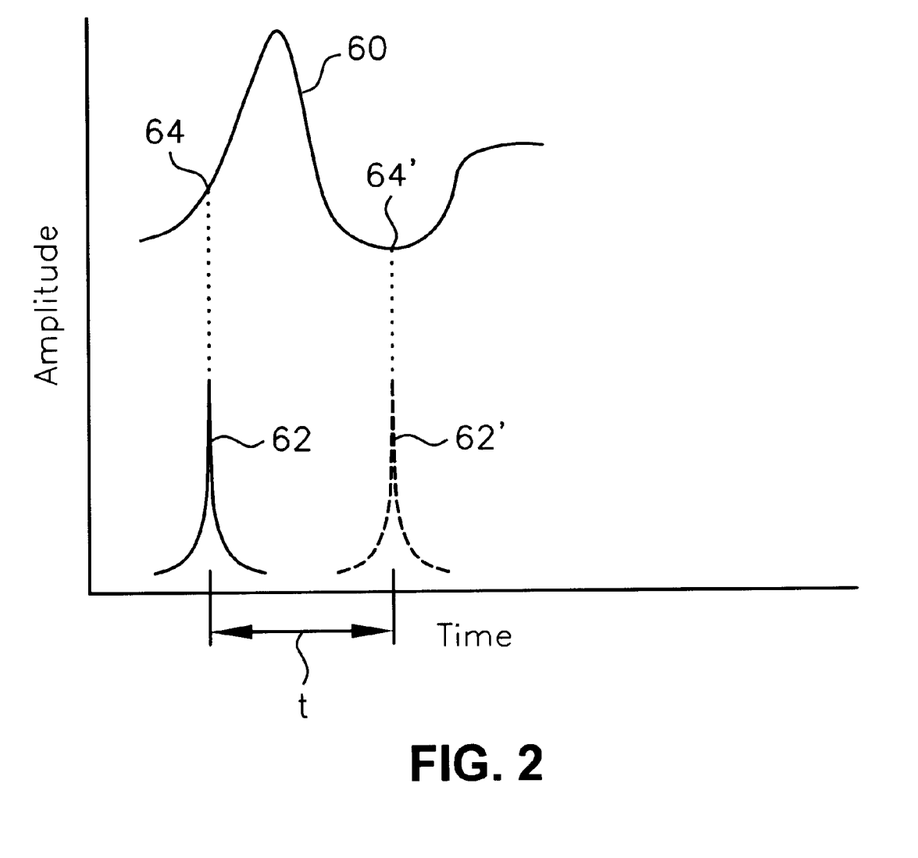
FIG. 2 is a plot of exemplary waveforms corresponding to the desired-frequency pulse and the probe pulse, showing the effect of changing the delay between the pulses.

Referring now to FIG. 2, there are shown an exemplary waveform 60 corresponding to output pulse 16 (having a long, GHz-THz wavelength) and waveforms 62 and 62' corresponding to probe pulse $P_2$ (having a shorter, typically optical, wavelength). The wavelength of probe pulse $P_2$ is detected by photo detectors 38A and 38B. Therefore, the information detected for any given length of delay stage 11 is limited to the information contained in the wavelength of probe pulse $P_2$. Because the wavelength of probe pulse $P_2$ (as illustrated by waveform 62 in FIG. 2) is much shorter than the wavelength of output pulse 16 (as illustrated by waveform 60 in FIG. 2) corresponding to the desired frequency to be studied, the information contained in waveform 62 is only representative of a single point 64 on waveform 60. By changing the pathlength of excitation pulse $P_1$, such as by varying the length of delay stage 11, the time-domain alignment of waveform 60 with respect to waveform 62 may be offset by a time delay, τ, as depicted by dashed waveform 62', thus providing another point 64' along waveform 60. Time delay τ is equal to Δl/c, where Δl is the change in optical path length and c is the speed of light.

Thus, information regarding the entire waveform 60 of output pulse 16 is obtained by changing the time delay between output pulse 16 and probe pulse $P_2$ over a plurality of lengths of delay stage 11 until a complete waveform 60 is characterized and stored electronically for a particular incident angle. The same information may be similarly derived by transmitting probe pulse $P_2$ through variable-length delay stage 11 instead of excitation pulse $P_1$.

Figure 3A:
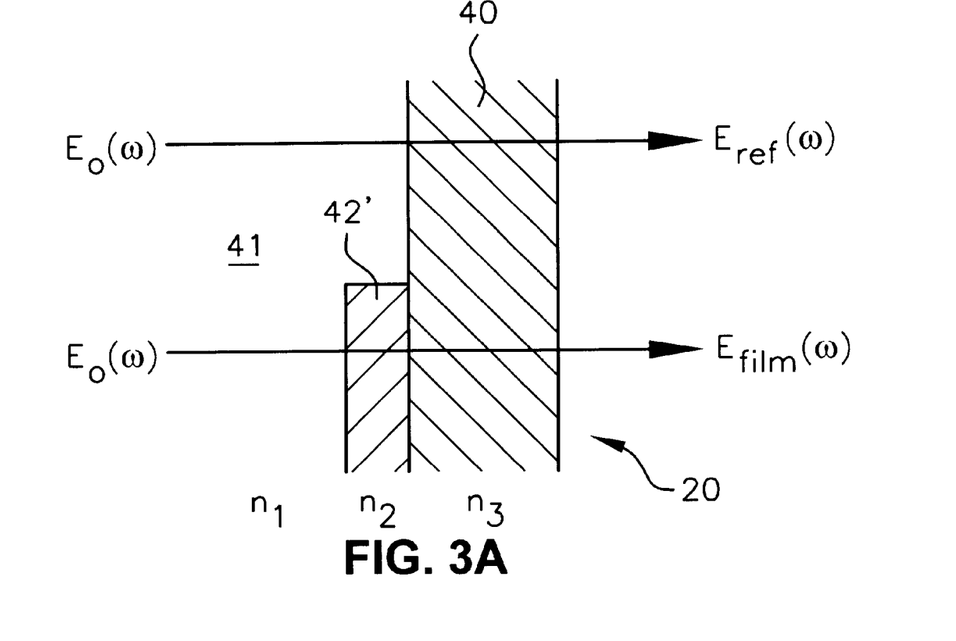
FIG. 3A is a cross-sectional illustration of sample 20 of FIG. 1, showing a substrate having a thin transmissive film layer and depicting the paths of pulse $E_0$ when the sample is in position B and position C as shown in FIG. 1.

Referring now to the cross-sectional schematic illustration of sample 20 in FIG. 3A, sample 20 comprises substrate 40 having thin film 42 with a thickness d on substrate 40. The indices of refraction for air 41, thin film 42, and substrate 40 are denoted by $n_1$, $n_2$, and $n_3$, respectively. The refractive index for a particular angular frequency ω is referred to as $n_2(\omega)$. For a free-standing thin film 42 not mounted on substrate 40, $n_1 = n_3$. The relationship between the index of refraction $n_2(\omega)$ and the dielectric constant $\kappa_2(\omega)$ is $\kappa_2(\omega) = n_2^2(\omega)$.

As described above, in the method of the subject invention, the input pulse ($E_0$) is fixed while sample 20 is moved in and out of the THz pulse. The designations $r_{ij}$ and $t_{ij}$ represent the reflection and transmission coefficients of the i→j interface (i, j=1, 2, 3 and i≠j), respectively. For example, $t_{23}$ is the transmission coefficient from thin film 42 to substrate 40.

The reference pulse can be expressed as:

$$E_{ref}(\omega) = t_{13} E_0(\omega) \exp(i\omega d/c). \qquad (1)$$

The phase in $E_{ref}(\omega)$ is referenced to the air-to-thin film (1→2) interface. Taking into account multiple reflections within the thin film, the field $E_{film}(\omega)$ has the form:

$$E_{film}(\omega) = \frac{t_{12} t_{23} \exp[i\delta(\omega) - \alpha(\omega)d]}{1 - r_{21} r_{23} \exp[2i\delta(\omega) - 2\alpha(\omega)d]} E_0(\omega), \qquad (2)$$

where $\alpha(\omega)$ is the amplitude absorption coefficient, $\delta(\omega)$ is the phase change of the field travelling through the film with $$\delta(\omega) = n_2(\omega) \omega d/c, \qquad (3)$$

c is the speed of light in vacuum, and i is the imaginary number $\sqrt{-1}$.

Unlike conventional TDS methods, where $E_{ref}(t)$ and $E_{film}(t)$ are each discretely measured in the time-domain, the DTDS method of the present invention measures $E_{ref}(t)$ and a differential signal $E_{diff}(t)$ defined as:

$$E_{diff}(t) = E_{film}(t) - E_{ref}(t). \qquad (4)$$

In the frequency-domain, which is derived by taking the Fourier transform of the time-domain signal, as is well-known in the art, the differential signal $E_{diff}(t)$ can be written as:

$$E_{diff}(\omega) = E_{film}(\omega) - E_{ref}(\omega). \qquad (5)$$

For a thin film, d<<c/ω, hence $\delta(\omega) << 1$. Under this approximation, we have:

$$\frac{E_{diff}(\omega)}{E_{ref}(\omega)} \approx i \frac{\omega}{c} d \left[ n_2 - 1 + \frac{(n_2 - n_1)(n_2 - n_3)}{(n_1 + n_3)} \right] - \alpha(\omega) d \left[ n_2 + \frac{(n_2 - n_1)(n_2 - n_3)}{(n_1 + n_3)} \right]. \qquad (6)$$

In principle, both $n_2(\omega)$ and $a(\omega)$ can be obtained from Eq. (6). For a high-quality dielectric film with a small loss tangent, the absorption can be neglected. When the thin film thickness is very small, $E_{diff}(t)$ is essentially proportional to the derivative of $E_{ref}(t)$. There is a π/2 phase difference between $E_{diff}(\omega)$ and $E_{ref}(\omega)$, therefore $n_2(\omega)$ is given by $|E_{diff}(\omega)/E_{ref}(\omega)|$.

Denoting $$A(\omega) \equiv \frac{c}{\omega d} \left| \frac{E_{diff}(\omega)}{E_{ref}(\omega)} \right|, \qquad (7)$$

Equations (6) and (7) lead to:

$$n_2(\omega) = \sqrt{(n_{1+n_3)(1+A(\omega))-n_{1n_3}}}. \qquad (8)$$

For a free-standing film ($n_1 = n_3 = 1$), Eq. (8) is simplified to:

$$n_2(\omega) = \sqrt{2A(\omega) + 1} \qquad (9)$$

Thus, Eq. (9) directly gives the refractive index $n_2(\omega)$ from the measured $A(\omega)$.

METHOD SUMMARY

Using the relationships derived above and sampling apparatus 10 as shown in FIG. 1, the thin film index of refraction at a desired frequency can be calculated by the method of the present invention. The method comprises generating input pulse $E_0$ having the desired frequency and probe pulse $P_2$ having a wavelength and duration shorter than the wavelength and duration of pulse $E_0$. Input pulse $E_0$ is directed along a path which intercepts sample 20 whereas probe pulse $P_2$ is directed along a path that does not intercept sample 20. Sample 20 is moved in and out of the path of input pulse $E_0$, creating output pulse 16. Output pulse 16 comprises a signal that alternates between transmitted signal $E_{film}(\omega)$, created by the input pulse being transmitted through sample 20 when sample 20 is in position B, and a reference signal $E_{ref}(\omega)$, created by the input pulse being transmitted through the free space and, optionally, substrate 40, such as when sample 20 is in position C. Probe pulse $P_2$ is then modulated by output pulse 16 in EO sensor 32, and the modulated probe pulse is detected using a photo detector. Differential signal $E_{diff}(\omega)$ is calculated in lock-in amplifier 37. The above steps are repeated over a plurality of delay times between input pulse $E_0$ and probe pulse $P_2$ until a complete field waveform of differential signal $E_{diff}(\omega)$ is characterized.

Figure 3B:
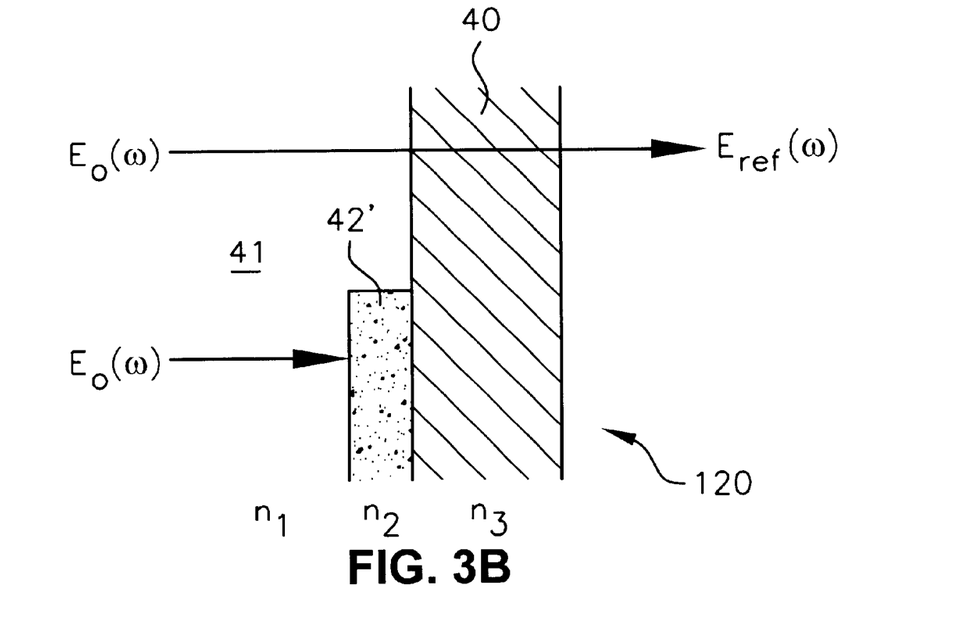
FIG. 3B is a cross-sectional illustration of reference plate 120, substituted for sample 20 of FIG. 1, showing a substrate having a non-transmissive thin film layer and depicting the paths of pulse $E_0$ when the reference plate is in position B and position C as shown in FIG. 1.

To characterize the reference signal $E_{ref}(\omega)$, the above steps are repeated again on the same sampling apparatus 10, but this time using a reference plate 120, as shown in FIG. 3B, which is identical to sample 20 except that thin film 42' is a non-transmissive film, such as aluminum, instead of being a thin transmissive film such as film 42. Substrate 40 is identical to the substrate of sample 20, if present in the sample. If sample 20 has no substrate, then reference plate 120 has no substrate. Thus, when using reference plate 120, output pulse 16 alternates between reference signal $E_{ref}(\omega)$, which comprises the input pulse transmitted through the free space (air 41), and optionally substrate 40, when non-transmissive thin film 42' is outside the input pulse path, and an absence of signal, created by the input pulse being blocked by non-transmissive thin film 42' when non-transmissive thin film 42' is in the input pulse path. Thus, the differential signal calculated by data acquisition system 39 for reference plate 120 is equal to the reference signal $E_{ref}(\omega)$.

The method then comprises calculating the index of refraction as a function of the ratio between the differential signal for the thin film and the reference signal, as expressed by Eq. (7) and Eq. (8) (or Eq. (7) and Eq. (9) when no substrate is present).

Because $E_{diff}(t)$ is measured in one measurement, rather than calculated by subtracting two separate measurements (with and without film) as with the conventional TDS, common noise is reduced so that the signal-to-noise ratio is improved over conventional TDS methods. To analyze the noise, the noise percentage of $E_{diff}(\omega)/E_{ref}(\omega)$ (left-side term of Eq. (6)) is expressed as:

$$\gamma \approx \left|\frac{\Delta E_{diff}(\omega)}{E_{diff}(\omega)}\right| + \left|\frac{\Delta E_{ref}(\omega)}{E_{ref}(\omega)}\right| \equiv \gamma_{diff}(\omega) + \gamma_{ref}(\omega), \quad (10)$$

where $\gamma_{diff}(\omega)$ and $\gamma_{ref}(\omega)$ are the noise percentage for the measurement of $E_{diff}(\omega)$ and $E_{ref}(\omega)$, respectively.

In conventional TDS methods, $E_{diff}(\omega)$ is obtained by subtracting $E_{film}(\omega)$ from $E_{ref}(\omega)$. If the film is very thin, $|E_{diff}(\omega)|<<|E_{ref}(\omega)|$ and $|\Delta E_{diff}(\omega)|\approx\sqrt{2}\Delta E_{ref}(\omega)|$, therefore the relative noise $\gamma_{diff}(\omega)>>\gamma_{ref}(\omega)$. Note, $$|E_{diff}(\omega)|\approx\phi(\omega)|E_{ref}(\omega)|, \quad (11)$$

with the film-induced phase $\phi(\omega)\equiv[n_2(\omega)-1]\omega d/c$. By using Eq. (11), Eq. (10) can be re-written as:

$$\gamma \approx \gamma_{ref}(\omega)[\sqrt{2}/\phi(\omega)+1] \quad (12)$$

When the phase change $\phi(\omega)$ decreases due to a decrease in the film thickness, the measurement error increases inversely proportionally to the phase change.

Because the measurement noise mainly comes from the differential signal $E_{diff}(\omega)$, the increased signal-to-noise ratio of $E_{diff}(\omega)$, as calculated using the method of the present invention, is ideal for the measurement of micron-thin films. Comparatively, for standard TDS methods comprising inserting a film into a THz beam and comparing the Fourier transforms of discrete THz waveforms obtained with and without the thin film, at 1 THz ($\phi$=0.004 radians), the relative noise $\gamma\approx355\gamma_{ref}$, according to Eq. (12). Therefore, even a relatively small $\gamma_{ref}$=1% results in $\gamma$=3.55.

Figure 6:
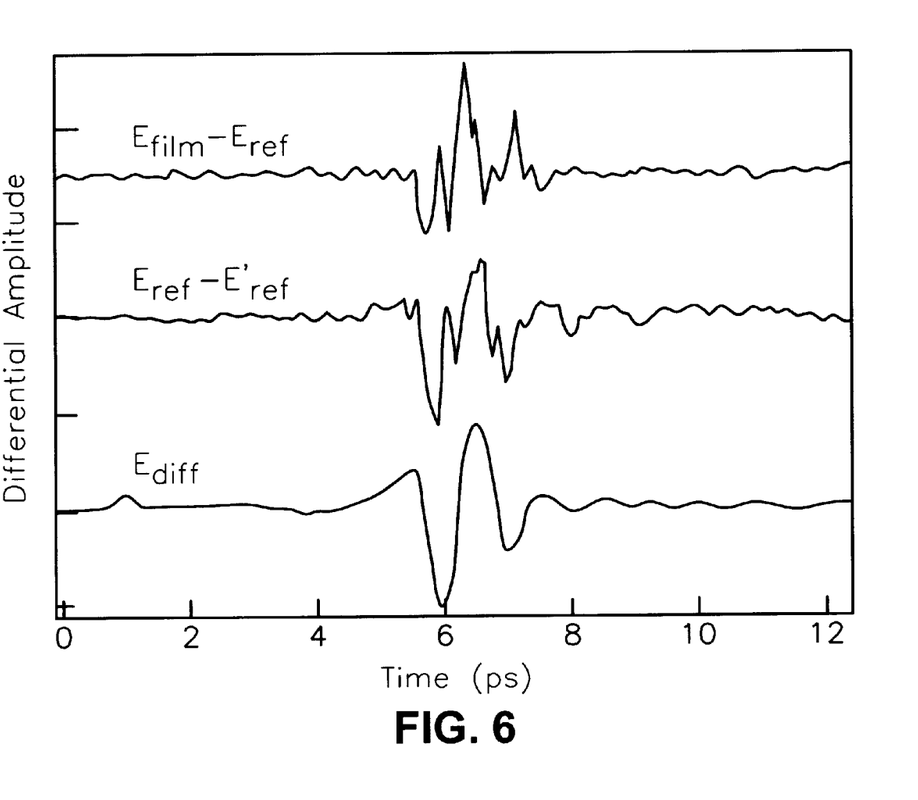
FIG. 6 graphically illustrates a waveform comparison in time (picoseconds) versus differential amplitude of the differential signal ($E_{diff}$)(DTDS) generated by the present invention (bottom), a differential signal ($E_{ref}$–$E'_{ref}$)(TDS) computed using two repeated reference waveforms generated by a conventional TDS method (middle), and a differential signal ($E_{film}$–$E_{ref}$)(TDS) computed using a waveform transmitted through a thin film and a reference waveform as generated by a conventional TDS method (top).

To illustrate the advantages of the differential method of the present invention for a 1.8 $\mu$m film, a differential waveform as measured by the method of this invention ($E_{diff}$)(DTDS), a differential waveform ($E_{film}$−$E_{ref}$)(TDS) computed using waveforms measured by a conventional TDS method, as well as a differential waveform computed using two repeated reference waveforms ($E_{ref}$−$E'_{ref}$)(TDS) measured by a conventional TDS method are plotted in FIG. 6. The reduced noise evident in the differential waveform produced by the method of this invention versus the curves produced by conventional TDS methods shows how the information relating to $n_2(\omega)$ can be obtained for such a small thin film by the method of this invention but not by conventional TDS methods.

In conventional TDS methods, $\gamma_{diff}(\omega)$ cannot typically be reduced by increasing the dynamic range of the reference signal because increasing the dynamic range does not decrease $\gamma_{ref}(\omega)$. Accordingly, for conventional TDS methods, the noise percentage in $E_{diff}(\omega)$ is bigger than in $E_{ref}(\omega)$ by a factor of $\sqrt{2}\Delta/\phi(\omega)$ that is always much larger than 1 for a thin film. In the method of this invention, however, $\gamma_{diff}(\omega)$ can be as small as $\gamma_{ref}(\omega)$, provided that there is a strong THz signal. In this sense, the method of this invention converts the large dynamic range into better signal-to-noise ratio.

The higher the dynamic range of the system, the stronger the differential signal $E_{diff}(t)$. Thus, the minimum measurable thickness of a free-standing film depends only on the system dynamic range. For thin film 42 on substrate 40, the minimum measurable thickness d depends on the uniformity of substrate 40 and the uniformity of thin film 42. If substrate 40 or thin film 42 is not uniform, this also contributes to the differential signal. For a THz system with an amplified laser having a dynamic range greater than $10^6$, the uniformities of substrate 40 and thin film 42 are typically the ultimate factors that limit the minimum measurable thickness of the thin film. All solid-state laser systems provide maximum stability for reduction of noise effects.

The present invention also offers advantages at relatively lower frequency measurements. By conventional TDS methods, low frequency measurement is time consuming because the phase change $\phi(\omega)$ is very small. For instance, for 100 GHz, the wavelength is 3 mm. For a film thickness of 10 $\mu$m, the phase change is only 1/600 wavelength with a refractive index of 1.5. Even if there is no noise at all, a fine step size (much less than 10 $\mu$m) and a long scanning range (much larger than 3 mm) are required to measure such a small phase change at such a low frequency, leading to a very long measuring time. With the method of the present invention, because the phase change is obtained by using the relative amplitude ratio $E_{diff}(\omega)/E_{ref}(\omega)$, the step size is determined only by the Nyquist sampling theorem. That is, the sampling frequency is preferably at least twice that of the maximum frequency of the signal. For example, if the maximum frequency is 2 THz, or equivalently 0.15 mm mechanical delay, then the sampling step size is preferably less than 0.15/2=0.075 mm. This step size is much larger than the film thickness.

Thus, the method of this invention greatly reduces the minimum measurable thickness over existing technology and is capable of providing dielectric constant measurement of sub-micron films at frequencies below 10 GHz.

The following example is included to more clearly demonstrate the overall nature of the invention. This example is exemplary, not restrictive, of the invention.

EXAMPLE

The reference waveform and the differential waveform at 0.7–1.2 THz for a free standing parylene-N (Pa-N) film with a thickness of 1.8 microns were derived using the method of the present invention. For this example, a model Coherent Rega 9000 mode-locked titanium:sapphire laser providing laser pulses with 800 nm central wavelength, 120 fs laser pulse duration, and 250 kHz repetition rate was used. A 2 mm thick <110> ZnTe crystal was used as the THz emitter via optical rectification. A galvanometer adapted to move the sample in and out of the pulse path at a frequency of 16 Hz was also used.

Figure 4:
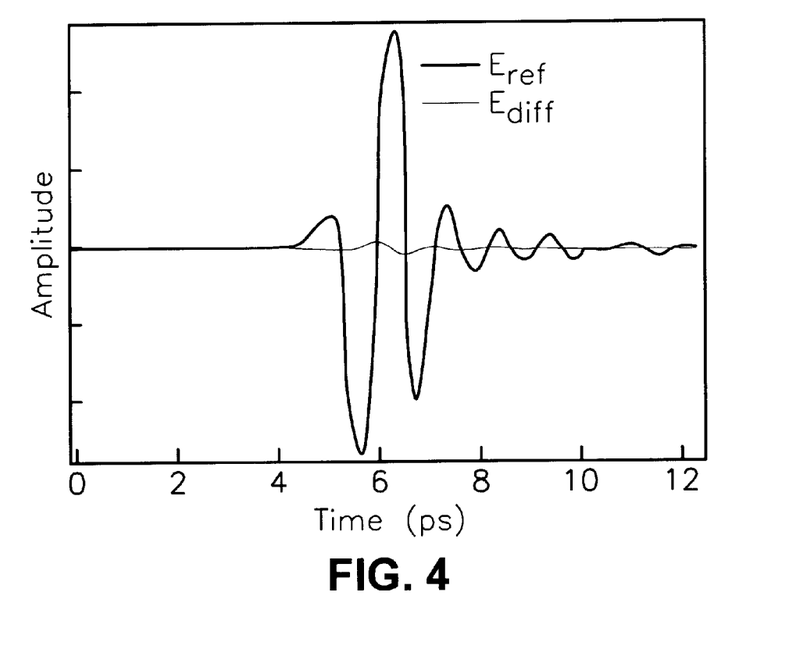
FIG. 4 shows a graphical comparison of an exemplary reference signal $E_{ref}$ and differential signal $E_{diff}$ as measured by the method of this invention in the 0.7–1.2 THz frequency range, plotted as time in picoseconds versus amplitude.
Figure 5:
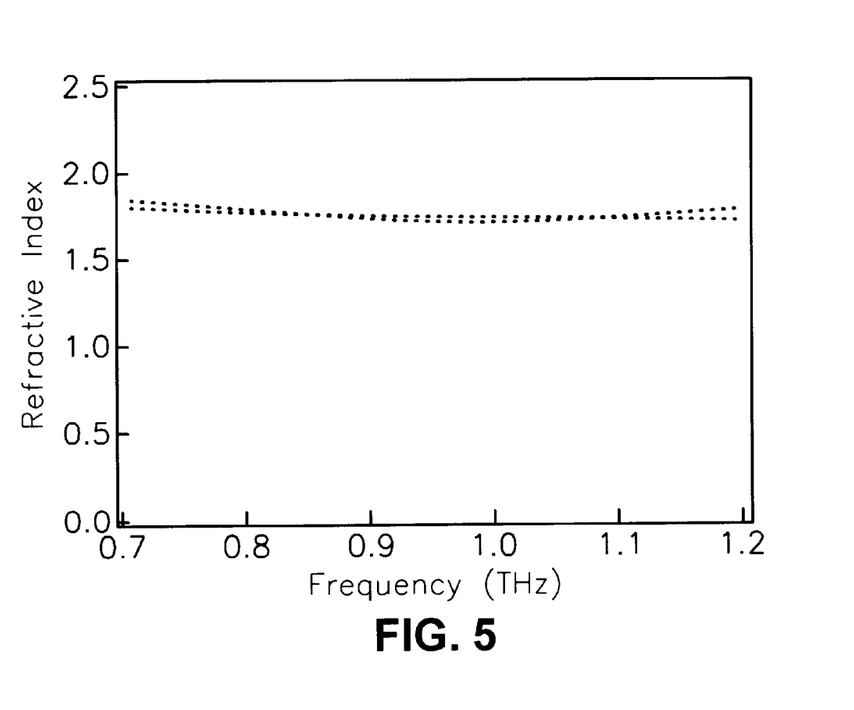
FIG. 5 shows a graph of frequency in the 0.7–1.2 THz range versus the refractive index for a 1.8 μm Parylene-N film as measured by an exemplary method of this invention.

A comparison of typical reference and differential waveforms in the 0.7–1.2 THz frequency range are plotted in FIG. 4. The differential signal is much smaller than the reference signal but is still measured with good signal-to-noise ratio. FIG. 5 shows the refractive index calculated from the experimental data using Equations (7) and (9). FIG. 5 shows the results from four repeated measurements, with the height of each data point roughly representing the measurement-to-measurement error.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A non-contact method for determining in a free space the index of refraction ($n_2(\omega)$) at a desired angular frequency ($\omega$) of a sample including a thin, transmissive film having a thickness (d) and optionally disposed on a substrate, the method comprising:

(a) generating (i) an input desired-frequency pulse having a first wavelength and a first duration, and (ii) a probe pulse having a second wavelength shorter than the first wavelength and a second duration shorter than the first duration;

(b) directing the input pulse along a first path and the probe pulse along a second path;

(c) moving the sample in and out of the first path, creating an output pulse which alternates between a transmitted signal ($E_{film}(\omega)$), created when the sample is in the first path, and a reference signal ($E_{ref}(\omega)$), created when the sample is outside the first path;

(d) modulating the probe pulse by the output pulse;

(e) detecting the modulated probe pulse with a photo detector;

(f) calculating a differential signal ($E_{diff}(\omega)$) for the thin film comprising a difference between the transmitted signal and the reference signal;

(g) repeating steps (a)–(f) over a plurality of delay times between the input pulse and the probe pulse until a complete field waveform of the differential signal for the thin film is characterized; and (h) calculating the index of refraction as a function of a ratio between the differential signal for the thin film and the reference signal.

2. The method of claim 1 further comprising, between steps (g) and (h), characterizing a complete field waveform of the reference signal by repeating steps (a)–(g) for a reference plate identical to the sample except comprising a non-transmissive film instead of the thin, transmissive film, the non-transmissive film mounted on an optional substrate identical to the sample optional substrate when present in the sample, such that in step (c) for the reference plate, the output pulse alternates between the reference signal ($E_{ref}(\omega)$), created when the non-transmissive film is outside the first path, and an absence of a signal, created when the non-transmissive film blocks the first path, such that in steps (f) and (g) for the reference plate, the differential signal for the non-transmissive film is equal to the reference signal.

3. The method of claim 1 wherein the function for the index of refraction comprises:

$$n_2(\omega) = \sqrt{(n_{1+n_3)(1+A(\omega))-n_{1n_3}}}$$

where:

$$A(\omega) = \frac{c}{\omega d}\left|\frac{E_{diff}(\omega)}{E_{ref}(\omega)}\right|$$

$n_1$ = index of refraction of the free space, and $n_3$ = index of refraction of the optional substrate.

4. The method of claim 1 wherein the desired-frequency pulse has a gigahertz to terahertz frequency.

5. The method of claim 4 wherein the desired-frequency pulse has frequency less than about 10 gigahertz.

6. The method of claim 1 wherein the probe pulse is optically detectable.

7. The method of claim 1 further comprising determining a dielectric constant for the thin film by calculating the index of refraction squared.

8. The method of claim 1 wherein:

step (a) comprises creating a first laser pulse and a second laser pulse, the first laser pulse being an excitation pulse that travels through a variable-length delay stage and impinges upon an emitter that becomes excited and emits the desired-frequency input pulse;

step (c) comprises moving the thin film in and out of the first path using a galvanometer;

step (d) comprises modulating the probe pulse by the output pulse using an electro-optical sensor to create an electro-optical resultant having a linear polarization;

between steps (d) and (e), the method further comprises circularly polarizing the electro-optical resultant with a quarter waveplate and linearly polarizing the circularly polarized electro-optical resultant in a prism which splits the resultant into a first detectable pulse and a second detectable pulse;

step (e) comprises detecting the first detectable pulse with a first photo detector and the second detectable pulse with a second photo detector and sending the pulses through circuitry which outputs noise-reduced electronic information;

step (f) comprises receiving the electronic information in a lock-in amplifier synchronized with the galvanometer to output electronic information corresponding to the differential signal;

step (g) comprises characterizing the complete waveform of the reference signal and the differential signal as time-domain signals, and step (h) comprises calculating a Fourier transform of the complete time domain waveforms of the reference signal and the differential signal to provide complete frequency-domain signals for use in calculating the index of refraction.

9. The method of claim 8 comprising directing a source laser pulse through a polarizer and a polarization beam splitter to produce the first pulse and the second pulse.

10. The method of claim 1 wherein the thin film has a thickness less than 2 $\mu$m.

* * * * *

UNITED STATES PATENT AND TRADEMARK OFFICE
CERTIFICATE OF CORRECTION

PATENT NO.    : 6,556,306 B2
DATED         : April 29, 2003
INVENTOR(S)   : Jiang et al.

It is certified that error appears in the above-identified patent and that said Letters Patent is hereby corrected as shown below:

Column 2,
Line 56, the equation should be $n_2(\omega) = \sqrt{(n_1 + n_3)(1 + A(\omega)) - n_1 n_3}$ Column 5,
Line 48, "co" should be -- $\omega$ --.

Column 6,
Line 50, the equation should be $n_2(\omega) = \sqrt{(n_1 + n_3)(1 + A(\omega)) - n_1 n_3}$ Column 8,
Line 29, the factor should be (without the "Δ") $\sqrt{2}/\varphi(\omega)$ Column 10,
Line 20, the equation should be $n_2(\omega) = \sqrt{(n_1 + n_3)(1 + A(\omega)) - n_1 n_3}$ Signed and Sealed this Twenty-third Day of September, 2003

JAMES E. ROGAN
*Director of the United States Patent and Trademark Office*